United States Patent [19]

Celmer et al.

[11] 4,032,632

[45] June 28, 1977

[54] MIXTURE OF ANTIBIOTICS PRODUCED BY NEW SPECIES OF STREPTOSPORANGIUM

[75] Inventors: Walter D. Celmer, New London; Walter P. Cullen, East Lyme; Charles E. Moppett, Mystic; John B. Routien, Lyme; Mark T. Jefferson, Waterford, all of Conn.; Riichiro Shibakawa, Handa; Junsuke Tone, Chita, both of Japan

[73] Assignee: Pfizer Inc., New York, N.Y.

[22] Filed: July 23, 1976

[21] Appl. No.: 708,181

[52] U.S. Cl. .............................. 424/121; 195/80 R
[51] Int. Cl.$^2$ ........................................ A61K 35/74
[58] Field of Search ................... 424/121; 195/80 R

[56] References Cited

UNITED STATES PATENTS 3,657,420  4/1972  Mancy et al. ..................... 424/121

Primary Examiner—Jerome D. Goldberg
Attorney, Agent, or Firm—Connolly and Hutz

[57] ABSTRACT

Two new species of Streptosporangium, designated *Streptosporangium koreanum* Routien sp. nov. and *Streptosporangium cinnabarinum* Routien sp. nov., when subjected to submerged aerobic fermentation, produce the same two new antibiotics. Methods for the recovery and purification of these antibiotics, co-produced with minor antibiotics, are described and some of their antimicrobial properties are outlined.

3 Claims, 2 Drawing Figures

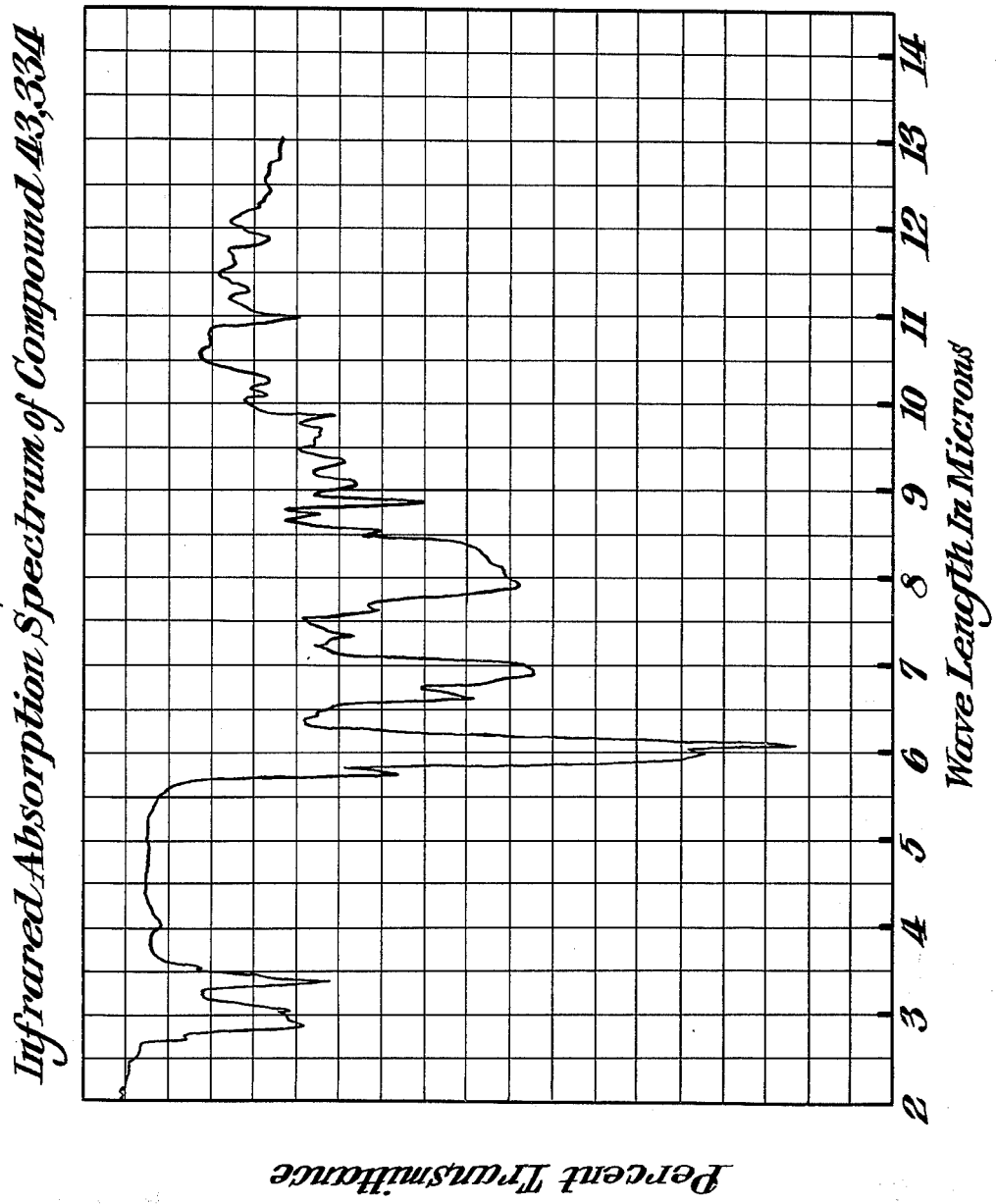

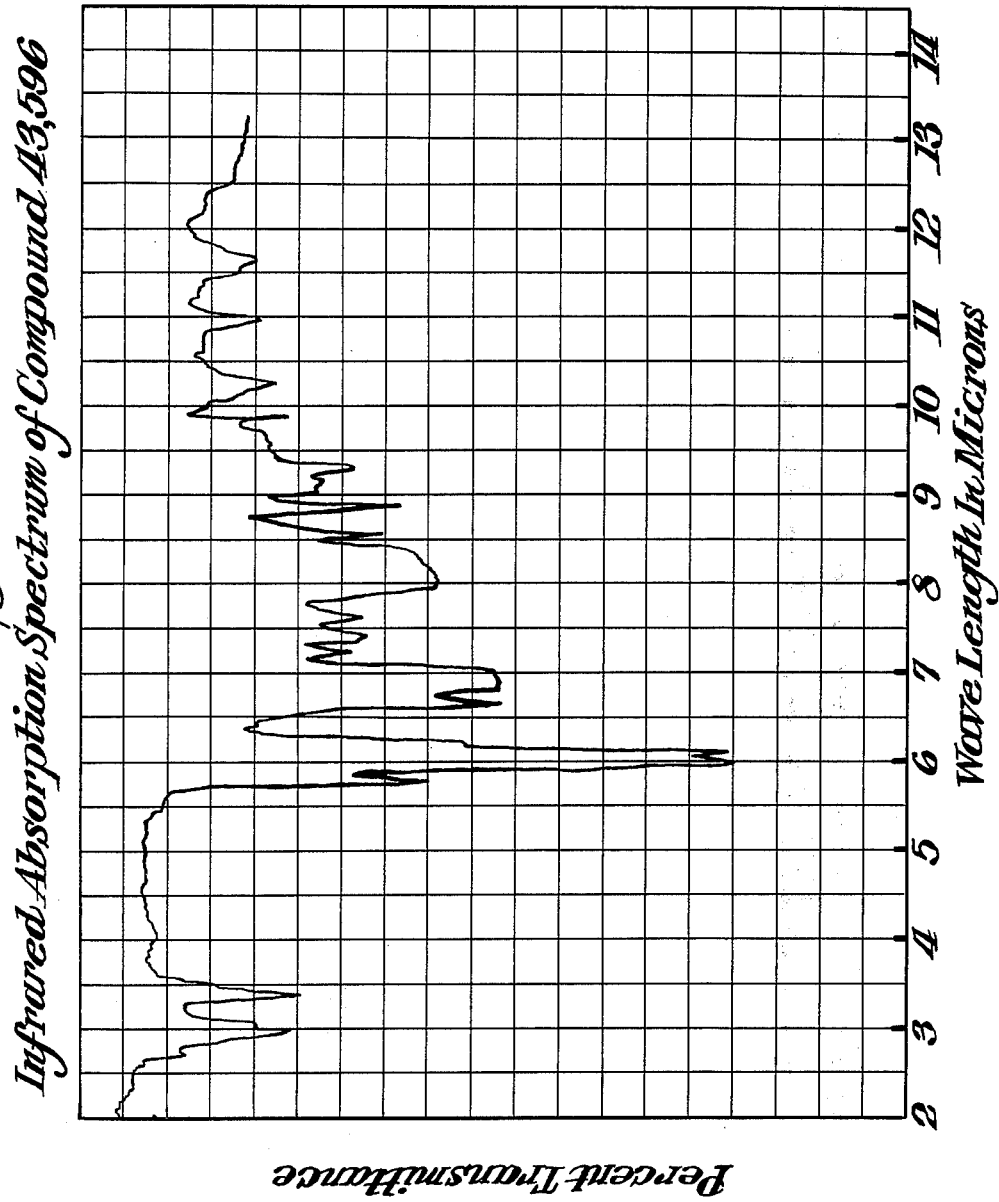

4,032,632

MIXTURE OF ANTIBIOTICS PRODUCED BY NEW SPECIES OF STREPTOSPORANGIUM

BACKGROUND OF THE INVENTION

The search for new antibiotics produced by soil microorganisms has encompassed the screening of various genera of bacteria, higher bacteria and fungi including many species within each genus and many strains within each species.

Among the microorganisms that are receiving increasing attention are those belonging to the genus Streptosporangium. This genus is differentiated from others belonging to the group of actinomycetes by the production of coiled chains of round to elliptical spores contained in sporangia and the production of aerial mycelium on the surface of the culture.

SUMMARY OF THE INVENTION

This invention is concerned with Compounds 43,334 and 43,596, new antibiotics produced under submerged aerobic fermentation conditions by *Streptosporangium koreanum* ATCC 31214 and *Streptosporangium cinnabarinum* ATCC 31213.

DETAILED DESCRIPTION OF THE INVENTION

*Streptosporangium koreanum* Routien sp. nov. (Pfizer F.D. 25492) and *Streptosporangium cinnabarinum* Routien sp. nov. (Pfizer F.D. 25488) have been deposited in The American Type Culture Collection, Rockville, Md. as the type cultures under their accession number ATCC 31214 and ATCC 31213, respectively. The permanency of the deposit and ready accessibility thereto by the public are afforded in the event the patent is granted. Access to the cultures is available during pendency of the application under Rule 14 and 35 USC 112. All restrictions on the availability to the public of the cultures deposited will be irrevocably removed upon granting of the patent.

Both cultures were prepared for planting on media by the method described in *Inter. Jr. Sys. Bacteriology* 16(3):322, 1966. The incubation temperature was 28° C. Readings of results were made at intervals up to 21 days. The colors of the cultures were made by comparison with chips from the Color Harmony Manual, fourth edition, as well as personal descriptive terms.

Identification media used for the characterization of the cultures and references for their composition are as follows:
1. Tryptone Yeast Extract Broth (ISP No. 1 medium, Difco).
2. Yeast Extract - Malt Extract Agar (ISP No. 2 medium, Difco).
3. Oatmeal Agar (ISP No. 3 medium, Difco).
4. Inorganic Salts - Starch Agar (ISP No. 4 medium, Difco).
5. Glycerol - Asparagine Agar (ISP No. 5 medium, Difco).
6. Peptone - Yeast Extract Iron Agar (ISP No. 6 medium, Difco).
7. Tyrosine Agar (ISP No. 7 medium, Difco).
8. Dextrose Nitrate Broth - S.A. Waksman, The Actinomycetes, Vol. 2, 1961, medium no. 1, p. 328 but with 3 g. glucose in place of sucrose and no agar.
9. Organic Nitrate Broth - R. E. Gordon and J. M. Mihm. Jr. Bact. 73:15-27, 1957.
10. Gelatin - Ibid.
11. Starch - Ibid.
12. Skim Milk - Difco.
13. Potato Carrot Agar - M. P. Lechevalier. Jr. Lab. and Clinical Med. 71:934–944, 1968 but use only 30 g. potatoes and 2.5 g. carrots and 20 g. agar.
14. 2% Tap Water Agar.
15. Glucose Asparagine Agar - S. A. Waksman, The Actinomycetes, Vol. 2, medium no. 2, p. 328, 1961.
16. Czapek - Sucrose Agar - Ibid, medium no. 1, p. 328.
17. Emerson's Agar - Ibid, medium no. 28, p. 331.
18. Nutrient Agar - Ibid, medium no. 14, p. 330.
19. Calcium Malate Agar - S. A. Waksman, Bact. Rev. 2101-29, 1957.
20. Cellulose - 
   a. H. L. Jensen. Proc. Linnean Soc. N. S. Wales 55:231-248, 1930.
   b. M. Levine and H. W. Schoenlein. A Compilation of Culture Media. 1930. Medium No. 2511.
21. Snake Skin Agar - A piece of dry snake skin about 2 × 1 inch in size was homogenized with 100 ml tap water in a blender. 2 g agar were added and the mixture was autoclaved.
21. Carbohydrate Utilization - 
   a. ISP No. 9, Difco.
   b. G. M. Luedemann and B. C. Brodsky. Antimicrobial Agents and Chemotherapy 1964:47. 1965.
22. Gauze's Medium No. 1 - G. F. Gauze et al., Problems in the Classification of Antagonistic Actinomycetes, 1959. p. 13.
23. Hemp Seed Culture - hemp seeds were boiled 30 min in water and then six or seven were added to a Petri dish containing a sterile salt solution devised by Machlis (R. Emerson in Mycologia 50:589-621, 1958 (p. 593)). A two-day old broth culture of F. D. 25488 was planted onto the hemp seeds. Incubation was at 28° C for 31 days before sporangia were found.

Pfizer culture (F.D. 25492) was concluded not to agree with the description of any known species of Streptosporangium. It is hereby described as new under the name *Streptosporangium koreanum* Routien sp. nov. The specific epithet refers to Korea where the soil sample yielding the culture was collected. F.D. 25492 as the type culture is deposited at the American Type Culture Collection with the accession number ATCC 31214.

The description of S. koreanum (F.D. 25492) follows:

Inorganic Salts Starch Agar - Growth very poor, colorless, scant spots of white aerial mycelium; reverse colorless; no soluble pigment.

Czapek - Sucrose Agar - Growth very poor, colorless, no aerial mycelium; reverse colorless; no soluble pigment.

Glucose - Asparagine Agar - Growth poor, slight yellow-cream (2 ca), no aerial mycelium; reverse like surface; no soluble pigment.

Glycerol - Asparagine Agar - Growth poor, thin, flat, colorless, no aerial mycelium; reverse colorless; no soluble pigment.

Calcium Malate Agar - Growth poor, thin, flat, colorless, few small tufts of white aerial mycelium; reverse not visible; no soluble pigment.

Emerson's Agar - Growth good, raised, roughened, no aerial mycelium, brownish-red (5 pe to 5 ne); reverse the same color as surface; red-brown soluble pigment.

Yeast Extract - Malt Extract Agar - Growth moderate, slightly raised and roughened, no aerial mycelium, reddish brown (5 ne); reverse the same color as the surface; pale reddish soluble pigment.

Nutrient Agar - Growth poor, small convex colonies, no aerial mycelium, dull and pale yellowish-green (2 ic); reverse the same color as the surface; no soluble pigment.

Oatmeal Agar - Growth moderate, flat, slightly raised, no aerial mycelium, reddish (5 nc); reverse the same color as the surface; pale red soluble pigment.

Starch Agar - Growth moderate, flat, no aerial mycelium, pale olive-brown (3 ne); reverse the same color as the surface; no soluble pigment.

Gelatin - Growth moderate, flat, no aerial mycelium, yellowish-green (3 pc to 3 pe); reverse the same color as the surface; no soluble pigment.

Potato-Carrot Agar - Growth poor to moderate, flat, no aerial mycelium, dull yellowish-green (3 pe); reverse the same color as the surface; pale pink soluble pigment.

Tap Water Agar - Growth poor, thin, flat, some white aerial mycelium, rest of streak colorless; reverse colorless; no soluble pigment.

Biochemical Properties - No melanin; weak production of $H_2S$ (lead acetate strips in air of peptone - yeast extract iron agar) in 7 days; nitrate reduced to nitrite in both media; weak hydrolysis of starch; weak liquefaction of gelatin; no change of skim milk even in 29 days; very slight growth without disintegration on cellulose in Levine and Schoenlein's medium in 29 days but no growth in Jensen's medium; Ca malate not digested; no soluble pigment on tyrosine; carbon utilization: no growth on any carbohydrate on ISP No. 9 medium; on Luedemann and Brodsky's medium: glucose, cellobiose, fructose, lactose, mannitol, mannose, melibiose, raffinose, starch, sucrose, trehalose and xylose utilized - adonitol, arabinose, dulcitol, galactose, glycerol, inositol, melezitose, rhamnose, ribose, salicin, sorbitol and sorbose not utilized.

Sporangia and Spores - Sporangia on tap water agar and snake-skin agar similar: round in surface view, 4.5–6.0$\mu$ wide on former and mostly 5.5–6.0$\mu$ but sometimes up to 8.0$\mu$ wide on latter, round to oval or slightly elliptical in profile, stalks 2.2–5.5$\mu$ tall on former but 3.0–8.0$\mu$ tall on latter medium.

Spores in coiled chains in sporangia, elliptical, 1.5–2.0 × 1.0–1.6$\mu$ wide to nearly round, 1.6$\mu$ wide.

This culture seemed to show certain similarities to *S. longisporum* on the basis of the description of the latter. The two cultures were therefore compared on a number of media at the same time. *S. longisporum* ATCC 25218, obtained from the American Type Culture Collection, was used for the comparison.

The two were distinctly different in that F.D. 25492 had larger colonies than did *S. longisporum*, color more orange than pink, a pinkish soluble pigment on two media versus no pigment and it reduced nitrate to nitrite whereas *S. longisporum* did not.

Pfizer culture (F.D. 25488), obtained from a soil sample from the Philippines, was found to be a strain of Streptosporangium different from any known species as well as F.D. 25492. It is, therefore, designated as a new species with the name Streptosporangium cinnabarinum Routien sp. nov. The specific epithet refers to the vermillion color of the growth on the two starch media used. Culture F.D. 25488 as the type culture is deposited at the American Type Culture Collection with the accession number ATCC 31213.

The description of *S. cinnabarinum* (F.D. 25488) follows:

Inorganic Salts Starch Agar - Growth good, vermillion (6 la), no aerial mycelium; reverse the same color as the surface; no soluble pigment.

Czapek - Sucrose Agar - Growth poor, slight yellow-cream (2 ca), no aerial mycelium; reverse the same color as the surface; no soluble pigment.

Glucose - Asparagine Agar - Growth moderate, slight yellow-cream (2 ca) in part of streak but pink at ends (5 ea to 6 ga), no aerial mycelium; reverse like surface in color; no soluble pigment.

Glycerol - Asparagine Agar - Growth moderate, flat, slightly pink, no aerial mycelium; reverse colorless to pale pink; no soluble pigment.

Calium Malate Agar - Growth moderate flat, yellow-green (2 ea), no aerial mycelium; reverse like surface in color; no soluble pigment.

Emerson's Agar - Growth excellent, raised, roughened, no aerial mycelium, orange red (5 na); reverse like surface in color; pale yellowish soluble pigment.

Yeast Extract - Malt Extract Agar - Growth good, raised, roughened, no aerial mycelium, yellowish-orange (3 ia to 3 lc); reverse like surface in color; no soluble pigment.

Nutrient Agar - Growth moderate, flat, smooth, pale pinkish-orange (hear 4 la), no aerial mycelium; reverse like surface in color; no soluble pigment.

Oatmeal Agar - Growth good, flat, no aerial mycelium, yellowish-orange with pink to salmon color at tips of streaks (2 nc to 3 nc in streak); reverse like streak in color; no soluble pigment.

Starch Agar - Growth good to excellent, raised, slightly roughened, no aerial mycelium, bright red to vermillion (near 6 pa); reverse like surface in color; no soluble pigment.

Gelatin - Growth good, slightly raised and with short radial furrows along margin of streak, no aerial mycelium, salmon-colored (5 ia to 5 ic); reverse like surface in color; no soluble pigment.

Potato-Carrot Agar - Growth moderate, flat, smooth, no aerial mycelium, pale pink (4 ea) at tip of streak, more yellowish in remainder of streak; reverse like surface in color; no soluble pigment.

Tap Water Agar - Growth poor, thin, flat, no aerial mycelium, colorless; reverse colorless; no soluble pigment.

Biochemical Properties - No melanin; strong production of $H_2S$ (on lead acetate strip in air of peptone - yeast extract iron agar) in 7 days; no reduction of nitrate to nitrite in 29 days in either medium; moderate hydrolysis of starch; moderate liquefaction of gelatin; no change of skim milk even in 29 days; good growth without disintegration on celulose in Jensen's medium but no growth in Levine and Schoenlein's; weak digestion of Ca malate; no soluble pigment on tyrosine; carbon utilization: on ISP No. 9 medium there were too many doubtful results; on Luedemann and Brodsky's medium: glucose, arabinose, cellobiose, fructose, galactose, inositol, mannitol, mannose, rhamnose, salicin, starch, sucrose, trehalose and xylose were utilized - adonitol, dulcitol, glycerol, lactose, melezitose, melibiose, raffinose, ribose, sorbitol and sorbose were not utilized.

Sporangia and Spores - On hemp seed culture after 31 days at 28° C sporangia were globose, 5–7.5$\mu$ wide; spores were globose to oval, 1.1–1.5$\mu$ to 1.3–1.6 × 1.1–1.3$\mu$.

Comparison of this culture with the descriptions of known species of Streptosporangium seemed to show some similarities to *S. vulgare*. As a result, the two cultures were compared at the same time on eight typical and varied media. *S. vulgare* CBS 433.61 was the strain of this species used for the study.

There was almost no resemblance between the two cultures. On Czapek-Sucrose and Glycerol-Asparagine Agars F.D. 25488 showed flatter and smoother growth than did S. vulgare and clearly had a pink vegetative mycelium in contrast to the other's creamy white (1½ ca to 2 ca).

On Inorganic - Salts Starch Agar F.D. 25488 was brilliant red to scarlet in color whereas *S. vulgare* was dull tan.

On Emerson's Agar F.D. 25488 was light orange (near 4 la) whereas S. vulgare was dull white from the thick, cerebriform growth.

On Oatmeal Agar F.D. 25488 was yellow (near 2 ia) with pale red color along a portion of the margin of growth; *S. Vulgare* showed some pale tan vegetative mycelium, but most of the growth was covered by a thin layer of white aerial mycelium bearing small numbers of sporangia with short stalks and measuring 4.5–6.0$\mu$ in width (very few sporangia appeared to be mature).

The cultures were alike in not reducing nitrate to nitrite in 14 days in either nitrate medium used.

Cultivaton of the *Streptosporangium* cultures preferably takes place in aqueous nutrient media at a temperature of 28°–36° C., and under submerged aerobic conditions with agitation. Nutrient media which are useful for such purposes include a source of assimilable carbon such as sugars, starch and molasses; source of organic nitrogen such as casein, enzymatic digest of casein, soybean meal, cottonseed meal, peanut meal and wheat gluten. A source of growth substances such as distillers' solubles, fish meal and yeast extract as well as salts such as sodium chloride and calcium carbonate and trace minerals such as iron, magnesium, zinc, cobalt and manganese may also be utilized with advantageous results. If excessive foaming is encountered during fermentation, antifoam agents such as vegetable oils or silicones may be added to the fermentation medium. Aeration of the medium in tanks for submerged growth is preferably maintained at the rate of about ½ to 2 volumes of free air per volume of broth per minute. Agitation may be maintained by means of agitators generally familiar to those in the fermentation industry. Aseptic conditions must, of course, be maintained through the transfer of the organism and throughout its growth.

Inoculum for the preparation of Compounds 43,334 and 43,596 may be obtained by employing growth from a slant of the culture on a medium such as ATCC Medium 172 (ATCC Catalogue, 10th edition, p. 235, 1972). The growth may be used to inoculate either shake flasks or inoculum tanks, or alternatively, the inoculum tanks may be seeded from the shake flasks. In shaken flasks growth will generally have reached its maximum in about 4 days whereas inoculum in submerged inoculum tanks will usually be at the most favorable period in 2 to 3 days. Substantial antibiotic activity is obtained in the final fermentor stage in approximately 40 to 60 hours.

The process of antibiotic production is conveniently followed during fermentation by biological assay of the broth employing a sensitive strain of *Staphylococcus aureus*. Standard plate assay technique is employed in which the zone of inhibition surrounding a filter paper disc saturated with the broth is used as a measure of antibiotic potency. After the fermentation broth has reached a desired level of antibiotic potency, the products are isolated from either whole broth or filtered broth. In the latter case, the mycelium is removed by filtration or centrifugation. Various types of equipment such as filter presses, centrifuges, etc. may be employed.

Thin-layer chromatography employing silica gel is a useful tool for analyzing the antibiotic mixture produced in fermentation media and the composition of crude and purified materials extracted from fermentation broths. The resolution of the components of the antibiotic mixture is importantly dependent on antibiotic loading of the system. Too little antibiotic potency fails to reveal minor antibiotic components; too much antibiotic potency results in a dragging effect with resulting poor resolution.

The developing system for the thin-layer chromatography is $CHCl_3$:$Me_2CO$ (1:1 v/v). The antibiotics may be visualized by exposure to 254 nm light, spraying with water which leads to water repellant spots or by overlaying with agar seeded with a sensitive strain of *Staphylococcus aureus*.

The components of the antibiotic complex may be separated and recovered from fermentation broth by solvent extraction, counter-current distribution, adsorption, column chromatography or combinations thereof. The antibiotics may be extracted from whole broth at a pH range of 4.0 to 10.0 employing an organic solvent such as butanol, pentanol, ethyl acetate, methylisobutyl ketone and other related water-immiscible solvents. The solvent is then concentrated under vacuum and the antibiotics precipitated by the addition of a solvent such as n-heptane.

The preferred method of separation and recovery of the components of the antibiotic complex is as follows: Whole fermentation broth (pH ca. 7.5) is extracted with methylisobutyl ketone. The solvent is removed in vacuo and the concentrate treated with about four volumes of n-heptane. The precipitated solids are collected by filtration, washed with n-heptane and dried in vacuo.

A portion of the crude antibiotic complex is dissolved in a minimum amount of ethyl acetate and treated with silica gel, preferably silica gel $PF_{254}$ (E. Merck, Darmstadt, Germany). The solvent is removed under vacuum and the residue treated with n-hexane to give a mobile slurry which is then added to a column of silica gel, preferably silica gel 60 (E. Merck, Darmstadt, Germany) topped with a bed of silica gel $PF_{254}$. The antibiotics are eluted with hexane, hexane:ethyl acetate-1:1 v/v, ethyl acetate and methanol. The fractions are monitored by means of thin-layer chromatography employing silica gel developed with chloroform:acetone-1:1 v/v. The antibiotics may be visualized by exposure to 254 nm light, spraying with water which leads to water repellant spots or overlaying with agar seeded with a sensitive strain of *Staphylococcus aureus*. The ethyl acetate fractions rich in Compound 43,334 are further processed by chromatography on silica gel $PF_{254}$, eluting with chloroform, chloroform:acetone (90:10% v/v), chloroform:acetone (80:20% v/v) and chloroform:acetone (50:50% v/v). The appropriate fractions are pooled and evaporated under vacuum to an amorphous solid.

Fractions rich in Compound 43,596 are rechromatographed on silica gel PF$_{254}$ eluting with chloroform, chloroform:acetone (50:50% v/v). Fractions enriched with Compound 43,596 are combined and further fractionated by preparative thin-layer chromatography. The apropriate band, after development with chloroform:acetone (50:50% v/v), is removed from the chromatogram and Compound 43,596 is eluted with chloroform:acetone (50:50% v/v). Following treatment with activated charcoal (Darco G60) in ethyl acetate solution, the antibiotic is precipitated as an amorphous white solid on addition of n-heptane.

On standing in solution in organic solvents (methanol in particular), Compound 43,334 undergoes a slow transformation to Compound 43,596. Convenient assays for monitoring this change are thin-layer chromatography or optical rotation. Whether Compound 43,596 is a true metabolite produced by the Streptosporangia cultures or is present solely because of its transformation from Compound 43,334 has not been resolved.

Compounds 43,334 and 43,596 are active against a variety of strains of *Staphylococcus aureus* and other Gram-positive bacteria including antibiotic-resistant strains. Table I illustrates the antibiotic spectra of the two antibiotics. These tests were run by seeding nutrient broth containing various concentrations of the pure antibiotics with the particular organism specified. The minimum inhibitory concentration (MIC) indicated in Table I is the minimum inhibitory concentration (in micrograms/ml) at which growth of the microorganism failed to occur.

Table I

| Organism | | MIC (mcg/ml) | |
|---|---|---|---|
| | | Compound 43,596 | Compound 43,334 |
| *Staphylococcus aureus* | 01A005 | 100 | 12.5 |
| | 01A052 | 100 | 25 |
| | 01A109 | 100 | 25 |
| | 01A110 | 50 | 3.13 |
| | 01A111 | >200 | 25 |
| | 01A087 | 200 | 25 |
| | 01A400 | 100 | 25 |
| *Streptococcus faecalis* | 02A006 | 100 | 6.25 |
| *Streptococcus pyogenes* | 02C203 | 12.5 | 0.78 |
| *Mycobacterium smegmatis* | 05A001 | 6.25 | 6.25 |
| *Bacillus subtilis* | 06A001 | 3.13 | 0.20 |

Significant protection is afforded to mice experimentally infected with *Staphylococcus aureus* 01A005 with Compounds 43,334 and 43,596 at subcutaneous doses of 600 to 1200 mg/kg.

Crude antibiotic complexes such as those obtained directly from broth or in any of the intermediate recovery stages as well as purified Compounds 43,334 and 43,596 may be employed in the treatment of antibiotic-sensitive infections in man and animals at parenteral doses of 200 to 1000 mg., depending on the type and severity of the infection and weight of the subject being treated. Solutions of Compounds 43,334 and 43,596 in sesame oil, peanut oil and/or propylene glycol at concentrations of 200 to 500 mg/ml may be employed for subcutaneous or intramuscular administration.

EXAMPLE I

A sterile aqueous medium having the following composition is prepared:

| Ingredient | Grams/liter |
|---|---|
| Glucose | 10 |

-continued

| Ingredient | Grams/liter |
|---|---|
| Starch | 20 |
| Yeast extract | 5 |
| Enzymatic digest of casein | 5 |
| Dipotassium hydrogen phosphate | 0.5 |
| Cobalt chloride | 0.002 |
| Calcium carbonate | 4 |
| Meat meal pH 7.1–7.2 | 5 |

Cells from a slant of *Streptosporangium koreanum* ATCC 31214 on ATCC medium 172 are transferred to a series of 300 ml flasks each containing 50 ml of this medium and shaken on a rotary shaker for 3–4 days at 28°–30° C. Aliquots of this grown inoculum are transferred to 300 ml flasks each containing 100 ml of the sterile medium grown above. After shaking for 3–4 days at 28°–30° C., 5–10% v/v the grown inoculum is transferred to a four liter fermentor containing two liters of the following sterile medium:

| Ingredient | Grams/liter |
|---|---|
| Glucose | 20 |
| Soy flour | 30 |
| Ferric sulfate | 0.3 |
| Manganese sulate | 0.3 |
| Calcium carbonate | 1 |
| Cobalt chloride | 0.002 |
| pH 7.2 ± 0.4 | |

The fermentation is conducted for 40 to 60 hours at 28° to 30° C. with stirring at 1700 revolutions/minute and aeration at about one volume of air per volume of broth per minute. The whole broth is twice extracted with ½ volumes of methylisobutyl ketone. The combined solvent extracts are concentrated under vacuum and the antibiotic activity precipitated by the addition of several volumes of n-heptane. The solids are collected by filtration or centrifugation.

EXAMPLE II

The method of Example I may be repeated employing *Streptosporangium cinnabarinum* ATCC 31213 in place of *Streptosporangium koreanum* ATCC 31214 and a fermentation medium of the following composition:

| Ingredient | Grams/liter |
|---|---|
| Glucose | 10 |
| Starch | 20 |
| Yeast Extract | 5 |
| Enzymatic digest of casein | 5 |
| Cobalt chloride | 0.002 |
| Calcium carbonate | 1 |

-continued

| Ingredient | Grams/liter |
|---|---|
| pH 7.2 ± 0.4 | |

EXAMPLE III

A large scale fermentation is conducted employing the inoculum and production media of Example I. A 250 gallon fermentor containing 100 gallons of medium, after being inoculated with a 5% v/v inoculum of *Streptosporangium koreanum* ATCC 31214, was run for 2 to 4 days at 30° C. with an aeration rate of one volume of air per volume of broth per minute. A 10% v/v inoculum from this fermentor was used to inoculate a 1500 gallon fermentor containing 1000 gallons of medium. The fermentor, after running for 2 to 3 days at 30° C. and an aeration rate of a volume of air per volume of broth per minute, was harvested by extracting the whole broth, without pH adjustment, with 1/5 volume of methylisobutyl ketone by means of a Podbielniak extractor. The solvent is concentrated under vacuum to a thin syrup, and the mixture of antibiotics precipitated by the addition of several volumes of n-heptane to yield 700 grams of solids.

A portion (75 grams) of the antibiotic complex is dissolved in the minimum volume of ethyl acetate and treated with 150 grams of silica gel 60 (E. Merck, Darmstadt, Germany). The solvent is removed under vacuum and the residue treated with n-hexane to give a mobile slurry which is then added to a sintered glass funnel containing 150 grams of silica gel 60 topped with a bed of 150 grams of silica gel $PF_{254}$ (E. Merck, Darmstadt, Germany). The antibiotics are eluted with hexane, hexane:ethyl acetate (1:1 v/v), ethyl acetate and methanol. All fractions are monitored by thin layer chromatography and appropriate fractions pooled. Those fractions (ethyl acetate, 15.1 grams) rich in Compound 43,334 are further processed by chromatography on silica gel $PF_{254}$ eluting with chloroform, chloroform:acetone (90:10% v/v), chloroform:acetone (80:20% v/v) and chloroform:acetone (50:50% v/v). Column fractions containing Compound 43,334 are pooled and the solvent removed under vacuum. The solids are dissolved in ethyl acetate and treated with activated charcoal (Darco G60). Following filtration and concentration under vacuum, Compound 43,334 is precipitated as an amorphous white solid by the addition of n-heptane. This material cannot be induced to crystallize.

Column cuts rich in Compound 43,596 are rechromatographed on silica gel $PF_{254}$ and developed with cloroform; chloroform-acetone (1:1 v/v). Column fractions rich in compound 43,596 are combined and further fractionated by means of preparative thin layer chromatography employing silica gel plates developed with chloroform:acetone (50:50% v/v). The appropriate band from each silica gel plate is eluted with chloroform:acetone (50:50% v/v). Following treatment with Darco G60 in ethyl acetate solution, Compound 43,596 is precipitated as a white amorphous solid by the addition of n-heptane. The antibiotic cannot be induced to crystallize.

Compound 43,334

Compound 43,334 does not have a definitive melting point. Analysis gives the following average proportions:

Carbon —60.63
Hydrogen —6.87
Nitrogen —10.42
Oxygen (by difference) —22.08

The compound is soluble in methanol, ethanol, chloroform, ethyl acetate, acetone and methylisobutyl ketone. It is insoluble in hexane, heptane and water.

Compound 43,334 is optically active having a rotation of $[\alpha]_D^{25°} = -73°$ (c = 1.0, MeOH).

The ultraviolet absorption maxima of Compound 43,334 in methanol are as follows:

$\lambda_{max}^{MeOH}$ 240$_{sh}$, 280 307 $_{sh}$ nm.
$E_{1\ cm}^{1\%}$ 95 47 26

The infrared spectrum of Compound 43,334 is shown in Figure 1. A chloroform solution shows characteristic absorption in the infrared region at the following wavelengths in microns: 2.95, 3.05, 3.12, 3.45, 5.79, 6.02, 6.13, 6.70, 7.04, 8.03, 8.92, 9.10 and 11.02.

Compound 43,596

Compound 43,596 does not have a definitive melting point. Analysis gives the following average proportions:

Carbon —60.19
Hydrogen —6.62
Nitrogen —10.21
Oxygen (by difference) —22.98

The compound is soluble in methanol, ethanol, chloroform, ethyl acetate, acetone and methylisobutyl ketone. It is insoluble in hexane, heptane and water.

Compound 43,596 is optically active having a rotation of $[\alpha]_D^{25°} = +116°$ (c = 1.0, MeOH).

The ultraviolet light absorption maxima of Compound 43,596 in methanol are as follows:

$\lambda_{max}^{MeOH}$ 287 302 nm.
$E_{1\ cm}^{1\%}$ 75 80

The infrared spectrum of Compound 43,596 is shown in FIG. 2. A chloroform solution shows characteristic absorption in the infrared region at the following wavelengths in microns: 3.03, 3.15, 3.47, 5.84, 6.03, 6.14, 6.70, 6.95, 7.50, 7.67, 8.07, 8.63, 8.90, 9.35, 10.30, 11.02 and 11.70.

What is claimed is:

1. An antibiotic complex produced by cultivating *Streptosporangium koreanum* Routien sp. nov. ATCC 31214 or *Streptosporangium cinnabarinum* Routien sp. nov. ATCC 31213 under submerged aerobic conditions in an aqueous nutrient medium containing an assimilable source of carbon and nitrogen until substantial antibiotic activity is obtained and separating said antibiotic complex therefrom.

2. Antibiotic substance Compound 43,334 which is soluble in methanol, ethanol, chloroform, ethyl acetate, acetone and methylisobutyl ketone; insoluble in hexane, heptane and water; has absorption maxima in methanol in the ultraviolet light region of the spectrum at 240, 280 and 307 nm with $E_{1\ cm}^{1\%}$ values of 95, 47 and 26, respectively; has the average composition by weight of 60.63% carbon, 6.87% hydrogen, 10.42% nitrogen and 22.08% oxygen (by difference); has an optical rotation of $\alpha_D - 73°$ (c = 1.0, methanol); and in chloroform solution exhibits characteristic absorption in the infrared region at the following wavelengths in microns: 2.95, 3.05, 3.12, 3.45, 5.79, 6.02, 6.13, 6.70, 7.04, 8.03, 8.92, 9.10 and 11.02.

3. Antibiotic substance Compound 43,596 which is soluble in methanol, ethanol chloroform, ethyl acetate, acetone and methylisobutyl ketone; insoluble in hexane, heptane and water; has absorption maxima in methanol in the ultraviolet light region of the spectrum at 287 and 302 nm with $E_{1\ cm}^{1\%}$ values of 75 and 80, respectively; has the average composition by weight of 60.19% carbon, 6.62% hydrogen, 10.21% nitrogen and 22.98% oxygen (by difference); has an optical rotation of $\alpha_D + 116°$ (c = 1.0, methanol); and in chloroform solution exhibits characteristic absorption in the infrared region at the following wavelengths in microns: 3.03, 3.15, 3.47, 5.84, 6.03, 6.14, 6.70, 6.95, 7.50, 7.67, 8.07, 8.63, 8.90, 9,35, 10.30, 11.02 and 11.70.

* * * * *